United States Patent [19]
Campbell, Jr.

[11] Patent Number: 5,886,117
[45] Date of Patent: *Mar. 23, 1999

[54] PROCESS USING BORANE DERIVED CATALYSTS FOR PREPARATION OF SYNDIOTACTIC VINYL AROMATIC POLYMERS

[75] Inventor: Richard E. Campbell, Jr., Midland, Mich.

[73] Assignee: The Dow Chemical Company, Midland, Mich.

[*] Notice: The portion of the term of this patent subsequent to Nov. 19, 2008, has been disclaimed.

[21] Appl. No.: 740,529

[22] Filed: Aug. 5, 1991

[51] Int. Cl.[6] ............................. C08F 4/643; C08F 12/04
[52] U.S. Cl. ......................... 526/134; 526/126; 526/131; 526/170; 526/293; 526/347.2
[58] Field of Search .................................... 526/131, 134, 526/170, 347.2, 126

[56] References Cited

U.S. PATENT DOCUMENTS 5,066,741  11/1991  Campbell, Jr. ..................... 526/346 X

*Primary Examiner*—Fred Teskin

[57] ABSTRACT

A process for preparing syndiotactic vinyl aromatic polymers comprising contacting at least one polymerizable vinyl aromatic monomer under polymerization conditions with a catalyst comprising a compound corresponding to the formula:

$$L_m MX_n^+ \ RA^-,$$

wherein:

L is a delocalized Π-bonding group containing up to 50 nonhydrogen atoms;

m is 0 or 1;

M is a metal of Group 4 of the Periodic Table;

X each occurrence is an inert, anionic ligand containing up to 20 nonhydrogen atoms;

n is an integer greater than or equal to 1 and the sum of m and n is one less than the valence of M; and $RA^-$ is $^-RB(C_6F_5)_3$, where R is hydride, hydrocarbyl, silyl, a combination thereof or a substituted derivative thereof having up to 20 nonhydrogen atoms. Also included is a process for preparing the catalyst.

12 Claims, No Drawings

PROCESS USING BORANE DERIVED CATALYSTS FOR PREPARATION OF SYNDIOTACTIC VINYL AROMATIC POLYMERS

BACKGROUND OF THE INVENTION

The present invention relates to a process for polymerizing vinyl aromatic monomers, such as styrene, to produce polymers having a high degree of syndiotacticity, and in particular to a process for preparing polymers of vinyl aromatic monomers having a high degree of syndiotacticity using an alkylalumoxane-free catalyst. More particularly still, this invention relates to such a process using catalyst compositions obtained by abstraction of a leaving group from inert Group 4 metal compounds with a borane. The resulting polymers may be usefully employed in the preparation of solid objects and articles such as a moldings, films, sheets and foamed objects by molding, casting or the like process.

In U.S. Pat. No. 4,680,353 there is disclosed a process for the preparation of polymers of vinyl aromatic monomers having a stereoregular structure of high syndiotacticity by the use of certain coordination catalysts. Particularly disclosed were the reaction products of a titanium compound and an organoaluminum compound, especially polymethylaluminoxane. The process disclosed in this patent requires the use of large amounts of the polymethylaluminoxane which is very expensive and difficult to make due to its very complex structure. Also, this process requires an expensive polymer purification system to remove remaining catalyst components due to the use of large amounts of the polymethylaluminoxane.

In EP 277,004 there are disclosed certain bis(cyclopentadienyl) metal compounds formed by reacting a bis(cyclopentadienyl) metal complex with salts of Bronsted acids containing a non-coordinating compatible anion. The reference discloses the fact that such complexes are usefully employed as catalysts in the polymerization of olefins.

In *J. Am. Ch. Soc.* 113, 3623–3625 (1991) there is disclosed a process for preparation of "cation like" zirconocene polymerization complexes by alkyl abstraction using tris(pentafluorophenyl)borane. The complexes were stated to have activity roughly comparable to typical zirconocene/alumoxane complexes.

SUMMARY OF THE INVENTION

According to the present invention there is now provided a process for preparing polymers of vinyl aromatic monomers having a high degree of syndiotacticity which process comprises contacting at least one polymerizable vinyl aromatic monomer under polymerization conditions with a catalyst comprising a metal complex corresponding to the formula:

$$L_mMX_n^+ RBY_3^-,$$

wherein:
L is a delocalized n-bonding group or substituted group containing up to 50 nonhydrogen atoms;
m is 0 or 1;
M is a metal of Group 4 of the Periodic Table;
X each occurrence is an inert, anionic ligand containing up to 20 nonhydrogen atoms;
n is an integer greater than or equal to 1 and the sum of m and n is one less than the valence of M;
R is hydrocarbyl, silyl, a combination thereof or a substituted derivative thereof, having up to 20 nonhydrogen atoms;
B is boron; and
Y is an inert covalently bound group having up to 40 atoms and $BY_3$ is a stable borane compound able to abstract an R group from a compound of the formula $L_mMX_nR$.

The preceding formula is referred to as the limiting, charge separated structure. However, it is to be understood that, particularly in solid form, the catalyst may not be fully charge separated. That is, the R group may retain a partial covalent bond to the metal atom, M. Thus, the catalysts may be alternately depicted as possessing the formula:

$$L_mMX_nRBY_3.$$

The catalysts are prepared by contacting a Group 4 metal containing compound of the formula:

$$L_mMX_nR$$

with the borane compound in an inert diluent. Alternatively, the catalysts may be prepared by contacting a Group 4 metal containing compound that is devoid of R groups with the borane compound in the presence of an aluminum compound of the formula $AlR_3$. Stated more explicitly the steps of this process comprise contacting a Group 4 metal containing compound of the formula:

$$L_mMX_{n+1}$$

with a borane compound of the formula $BY_3$ in the presence of an aluminum compound of the formula $AlR_3$ in an inert diluent under conditions to cause abstraction of at least one R group from the aluminum compound and assimilation thereof in the resulting borane containing complex.

DETAILED DESCRIPTION OF THE INVENTION

As used herein, the term "syndiotactic" refers to polymers having a stereoregular structure of greater than 50 percent syndiotactic of a racemic triad as determined by $C^{13}$ nuclear magnetic resonance spectroscopy. Such polymers may be usefully employed in the preparation of articles and objects (e.g., via compression molding, injection molding or other suitable technique) having an extremely high resistance to deformation due to the effects of temperature.

The term "substituted" when used with reference to L or R means inert substituent groups, including such groups as aralkyl, alkaryl, haloalkyl, silylalkyl, haloalkyl, haloaryl, haloalkaryl, halosilyl, haloalkarylsilyl, alkoxyalkyl, and so forth.

The term "inert" means noninterfering with the desired catalyst preparation or with the use of the resulting metal complex containing compound as a polymerization catalyst.

All reference to the Periodic Table of the Elements herein shall refer to the Periodic Table of the Elements, published and copyrighted by CRC Press, Inc., 1989. Also, any reference to a Group or Series shall be to the Group or Series as reflected in this Periodic Table of the Elements, utilizing the IUPAC system for numbering groups.

Preferred compositions according to the present invention are those wherein m is 1, n is 2, and L is a cyclopentadienyl or substituted cyclopentadienyl group. Examples of cyclopentadienyl and substituted cyclopentadienyl groups for use according to the present invention are groups depicted by the formula:

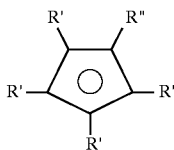

wherein:

R' each occurrence is independently selected from the group consisting of hydrogen, halogen, R, N—$R_2$, P—$R_2$; OR; SR or $BR_2$, wherein R is as previously defined. Preferably, R' is alkyl or haloalkyl of up to 6 carbons. Preferred delocalized n-bonding groups are cyclopentadiene and substituted cyclopentadiene, especially pentamethylcyclopentadiene.

Most preferably M is titanium.

Illustrative but nonlimiting examples of X include R, halo, $NR_2$, $PR_2$, OR, SR, $BR_2$, etc. Preferably X each occurrence is R, $NR_2$ or OR.

Illustrative, but not limiting examples of suitable metal derivative compounds include: tetranorborene titanium, tetrabenzyl zirconium, tetraneopentyl titanium, (cyclopentadienyl)dimethyl-(isopropoxy)titanium, (cyclopentadienyl)dibenzyl-(isopropoxy)titanium, (cyclopentadienyl)dibenzyl-(phenoxy)zirconium, (cyclopentadienyl)dibenzyl-(isopropoxy)hafnium, (cyclopentadienyl)dimethylzirconium chloride, bis(phenoxy)di(trimethylsilyl)zirconium, phenoxytrimethylzirconium, bis(2,6-diisopropyl-4-methyl)phenoxy)dibenzyltitanium, bis(2,4,6-trimethylphenoxy)dibenzyltitanium, tri(tertiary-butyl)siloxytrimethyl zirconium, bismethoxydi-(phenylmethyl)titanium, bis(2,4,6-trimethylphenoxy)dibenzyltitanium, triphenoxybenzyltitanium, butoxytris((trimethylsilyl)methyl)zirconium, dimethoxydimethylzirconium, 4-(1-methyl-1-(4-methoxyphenyl)ethyl)phenoxy tribenzyl titanium, dinorborene dichlorotitanium, tribenzyltitanium hydride, cyclopentadienyltribenzylzirconium, cyclopentadienyltribenzyltitanium, cyclopentadienyltrimethyltitanium, cyclopentadienyltrimethylzirconium, cyclopentadienyltrineopentyltitanium, cyclopentadienyltri(diphenylmethyl)zirconium, cyclopentadienyltriphenylzirconium, cyclopentadienyltrineopentylzirconium, cyclopentadienyltri(m-tolyl)zirconium, cyclopentadienyltri(p-tolyl)zirconium, cyclopentadienyldimethyltitanium hydride, cyclopentadienyltri(diphenylmethyl)zirconium, pentamethylcyclopentadienyltrimethylzirconium, ethylcyclopentadienyltrimethylzirconium, pentamethylcyclopentadienyltribenzylzirconium, n-butylcyclopentadienyltrineopentyltitanium, (t-butylcyclopentadienyl)tri(trimethylsilyl)zirconium, cyclohexylcyclopentadienyltrimethylzirconium, (pentamethylcyclopentadienyl)dimethylzirconium chloride, indenyldibenzyltitanium chloride, (pentamethylcyclopentadienyl)diisopropoxy hafnium chloride, (benzylcyclopentadienyl)di(m-tolyl)titanium chloride, (diphenylcyclopentadienyl)dinorborneylzirconium chloride, pentamethylcyclopentadienyltriphenylzirconium, tetraethylcyclopentadienyltribenzylzirconium, propylcyclopentadienyltrimethylzirconium, propylcyclopentadienyltrimethylzirconium, (n-butylcyclopentadienyl)dimethyl(n-butoxy)titanium, cyclopentadienyldiphenylisopropoxyzirconium, cyclohexylmethylcyclopentadienyltribenzylzirconium, cyclohexylmethylcyclopentadienyltrimethylzirconium, cyclopentadienylmethylzirconium dihydride, benzylcyclopentadienyltrimethylhafnium, indenyltribenzylzirconium, trimethylsilylcyclopentadienyltrimethylzirconium, trimethylgermylcyclopentadienyl)trimethyltitanium, trimethylstannylcyclopentadienyltribenzylzirconium, (pentatrimethylsilyl)cyclopentadienyltrimethylzirconium, trimethylsilylcyclopentadienyltrimethylzirconium, penta (trimethylsilyl)cyclopentadienyltribenzyltitanium, trimethylgermylcyclopentadienyltriphenylhafnium, trifluoromethylcyclopentadienyltrimethylzirconium, trifluoromethylcyclopentadienyltrinorborneylzirconium, trifluoromethylcyclopentadienyltribenzylzirconium, cyclopentadienyltrimethylsilylzirconium, cyclopentadienyltri(phenyldimethylsilyl)zirconium, and the like.

Other compounds which are useful in the catalyst compositions of this invention will, of course, be apparent to those skilled in the art.

Suitable borane compounds for use herein particularly include tris(fluoroaryl) and tris (trifluoromethyl substituted aryl) borane compounds, or other suitable inertly substituted borane compounds. Examples include tris (pentafluorophenyl)borane, tris(tetra-2,3,5,6-tetrafluorophenyl)borane, tris(3,5-di(trifluoromethyl)phenyl)borane, etc. Especially preferred are perfluorinated compounds such as tris(pentafluorophenyl)borane.

In general, the catalyst can be prepared by combining the metal compound and borane compound (or by combining the metal compound, borane compound and $AlR_3$) in a suitable solvent at a temperature within the range from about −100° C. to about 300° C. The presence of residual aluminum containing species in the catalyst system is not detrimental to catalyst performance. The catalyst system can also form in situ if the components thereof are added directly to the polymerization process and a suitable solvent or diluent, including condensed monomer, is used in said polymerization process. It is, however, preferred to form the catalyst in a separate step in a suitable solvent prior to adding the same to the polymerization step. The catalysts' components are generally sensitive to both moisture and oxygen and should be handled and transferred in an inert atmosphere such as nitrogen, argon or helium.

When the catalysts of the invention are prepared by combining the metal compound, borane compound and $AlR_3$ it is believed that a transfer of one or more R groups to the metal compound first occurs. Upon interacting with the borane compound, one of the R groups is then abstracted by the borane to form the ultimate catalytic species. Thus by this technique the metal compound initially utilized may be a metal alkoxide or similar compound which by itself would not be suitable for use in combination with the borane.

As previously indicated, the improved catalyst of the present invention will, preferably, be prepared in a suitable solvent or diluent. Suitable solvents or diluents include any of the solvents known in the prior art including, but not necessarily limited to, straight and branched-chain hydrocarbons such as $C_{6-12}$ alkanes (hexane, heptane, octane and the like); $C_{6-12}$ cyclic and alicyclic hydrocarbons such as cyclohexane, cycloheptane, methylcyclohexane, methylcycloheptane and the like and $C_{6-12}$ aromatic and alkyl-substituted aromatic compounds such as benzene, toluene, xylene, decalin, and the like, and mixtures thereof.

In general, catalysts according to the present invention can be selected so as to produce polymer products that will be free of certain trace metals generally found in polymers produced with Ziegler-Natta type catalysts containing cocatalysts such as aluminum or magnesium based compounds.

In the practice of the present invention, vinyl aromatic monomers can be polymerized in the presence of the catalyst as mentioned above. Suitable vinyl aromatic monomers which can be polymerized in the process of the present invention include those represented by the formula:

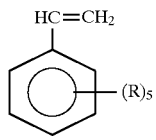

wherein each R is independently hydrogen; an aliphatic, cycloaliphatic or aromatic hydrocarbon group having from 1 to 10, more suitably from 1 to 6, most suitably from 1 to 4, carbon atoms; or a halogen atom. Examples of such monomers include, styrene, chlorostyrene, n-butyl styrene, p-vinyl toluene etc. with styrene being especially suitable. Copolymers of styrene and the above vinyl aromatic monomers other than styrene can also be prepared.

The polymerization may be conducted under slurry, bulk or suspension polymerization conditions or other suitable reaction conditions including solid, powdered reaction conditions. The polymerization can be conducted at temperatures of from 0° C. to 160° C., preferably from 25° C. to 100° C., more preferably from 30° C. to 80° C., for a time sufficient to produce the desired polymer. Typical reaction times are from one minute to 100 hours, preferably from 1 to 10 hours. The optimum reaction time or reactor residence time will vary depending upon the temperature, solvent and other reaction conditions employed. The polymerization can be conducted at subatmospheric pressure as well as superatmospheric pressure, suitably at a pressure within the range of 1 to 500 psig (6.9 kPa–3,400 kPa). The use of ambient or low pressures, e.g., 1–5 psig (6.9–34.5 kPa) is preferred in view of lower capital and equipment costs.

The polymerization may be conducted in the presence of an inert diluent or solvent or in the absence thereof, i.e., in the presence of excess monomer. Examples of suitable diluents or solvents include $C_{6-20}$ aliphatic, cycloaliphatic, aromatic and halogenated aliphatic or aromatic hydrocarbons, as well as mixtures thereof. Preferred diluents comprise the $C_{6-10}$ alkanes, toluene and mixtures thereof. A particularly desirable diluent for the polymerization is iso-octane, iso-nonane or blends thereof such as Isopar-E®, available from Exxon Chemical Company. Suitable amounts of solvent are employed to provide a monomer concentration from 5 percent to 100 percent by weight.

The molar ratio of the vinyl aromatic monomer to the catalyst (in terms of metal) may range from 100:1 to 1,000,000:1, preferably from 3,500:1 to 200,000:1. In the case of using a solvent, the catalyst may be used at a concentration with the range from about $10^{-7}$ to about $10^{-1}$ moles per liter of solvent.

As in other similar polymerizations it is highly desirable that the monomers and solvents employed be of sufficiently high purity that catalyst deactivation does not occur. Any suitable technique for monomer purification such as devolatilization at reduced pressures, contacting with molecular sieves or high surface area alumina, deaeration, etc. may be employed. In addition a small amount of an aluminum trialkyl compound or similar scavenger may be added to the reaction mixture to protect the catalyst from deactivation by contaminants in the reaction mixture.

Purification of the resulting polymer to remove entrained catalyst may also be desired by the practitioner. Purification of the resulting polymer prepared by the process of this invention is much easier than a conventional process since the process of this invention does not use polyalkylaluminoxane which is used in large quantities as cocatalyst in the conventional process. Entrained catalyst may generally be identified by residues of ash on pyrolysis of the polymer that are attributable to catalyst metal values. A suitable technique for removing such compounds is by solvent extraction, e.g., extraction utilizing hot, high boiling chlorinated solvents, acids or bases such as caustic followed by filtration. However because of the small amounts of catalyst used in the process, polymer clean up is normally not necessary.

Having described the invention, the following examples are provided as further illustrative and are not to be construed as limiting. Unless stated to the contrary, all parts and percentages are based on weight.

EXAMPLE 1

Preparation of Catalyst

A dry 2 ml volumetric flask was charged with 0.70 ml of a 0.0069M toluene solution of pentamethylcyclopentadienyltitanium tribenzyl under an argon atmosphere. Next, 97 μl of a 0.05M solution of tri(pentafluorophenyl) boron in toluene was added. Additional toluene was added to fill the flask. The contents were stirred for one hour at 25° C. resulting in the formation of a medium, red-brown, 0.00241M solution of a composition having a charge separated, limiting structure corresponding to the formula:

wherein Cp is cyclopentadienyl and Bz is benzyl.

Preparation of Syndiotactic Polystyrene

A dry 20 ml vial was charged with 10.0 ml (87.4 mmol) of purified styrene and 20 μl of a 1M solution of triisobutyl aluminum in toluene. The vial was capped with a teflon coated septa and a metal crimp cap, and placed in a water bath at 70° C. After 10 minutes 250 μl of the above catalyst composition was added, giving a total molar ratio of styrene:Ti:borane:triisobutyl aluminum of 145,000:1:1:33. After 1 hour the vial was removed from the water bath and the polymerization was stopped by the addition of 2 ml of methanol. The off-white, insoluble product was washed with methanol and dried in-vacuo to obtain 5.2 gm of a resultant polymer. The polymer was insoluble in methylene chloride or other common solvents for atactic polystyrene, and had a melting point of 270.4° C. (by DSC), consistent with polystyrene having a syndiotacticity of greater than 98 percent. Yield was 0.45 g, 5.0 percent. Molecular weight (Mw) determined by viscosity comparison of o-dichlorobenzene solutions was 221,000.

EXAMPLE 2

The reaction conditions of Example 2 were repeated excepting that the titanium compound used was pentamethylcyclopentadienyltrismethoxy titanium (4.8 μmol) and 26.5 μl of a 1M toluene solution of triisobutyl aluminum was added to the titanium compound before addition of the borane solution. The mixture of titanium compound, triisobutyl aluminum and tri(pentafluorophenyl)borane was allowed to interact while being stirred for 1.5 hours. The resulting catalyst solution was a medium brown color. The polymerization conditions of Example 1 were substantially repeated. The resulting polymer had a crystalline melting point of 270.2° C., consistent with a polymer having greater than 98 percent syndiotacticity. Yield was 11.5 percent. Mw as determined by viscosity comparison techniques was 814,000.

Comparative

When the above reaction conditions were repeated without addition of the triisobutyl aluminum solution, no polymerization occurred.

EXAMPLE 3

The reaction conditions of Example 2 were substantially repeated excepting that 48 μl of a 1M toluene solution of triisobutyl aluminum was added to the pentamethylcyclopentadienyltrismethoxy titanium compound before addition of the borane solution. In addition 1.25 ml of the 0.05M solution of tri(pentafluorophenyl) borane was used. The mixture of titanium compound, triisobutyl aluminum and tri(pentafluorophenyl)borane was allowed to interact while being stirred for 1.5 hours. The resulting catalyst solution was a medium brown color. The polymerization conditions of Example 3 were also repeated. The final molar ratio of styrene: Ti:borane:triisobutyl aluminum was 145,000:1:13:43. The resulting polymer had a crystalline melting point of 269.6° C., consistent with a polymer having greater than 98 percent syndiotacticity. Yield was 8.3 percent. Mw was 763,000.

What is claimed is:

1. A process for preparing polymers of vinyl aromatic monomers having a high degree of syndiotacticity comprising contacting at least one polymerizable vinyl aromatic monomer under polymerization conditions with a catalyst comprising a metal complex corresponding to the formula:

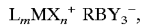

$L_mMX_n^+ \, RBY_3^-$, wherein:

L is a delocalized Π-bonding group or substituted group containing up to 50 nonhydrogen atoms;

m is 0 or 1;

M is a metal of Group 4 of the Periodic Table;

X each occurrence is an inert, anionic ligand containing up to 20 nonhydrogen atoms;

n is an integer greater than or equal to 1 and the sum of m and n is one less than the valence of M;

R is hydrocarbyl, silyl, a combination thereof or a substituted derivative thereof having up to 20 nonhydrogen atoms;

B is boron; and

Y is an inert covalently bound group having up to 40 atoms and $BY_3$ is a stable borane compound able to abstract an R group from a compound of the formula $L_mMX_nR$.

2. The process according to claim 1 wherein the monomer is contacted with the catalyst at a temperature from 0° C. to 160° C.

3. The process according to claim 1 wherein the monomer is contacted with the catalyst at a pressure of from about 1 to about 500 psig.

4. The process according to claim 1 wherein the monomer is contacted with the catalyst for from one minute to 100 hours.

5. The process according to claim 1 wherein the monomer is contacted with the catalyst in the presence of a solvent.

6. The process according to claim 5 wherein the solvent is selected from the group consisting of $C_{6-20}$ aliphatic, cycloaliphatic, aromatic, halogenated aliphatic, halogenated aromatic hydrocarbons and mixtures thereof.

7. The process according to claim 1, wherein the molar ratio of the vinyl aromatic monomer to the catalyst ranges from 100:1 to 1,000,000:1.

8. The process according to claim 1 wherein the vinyl aromatic monomer is represented by the formula:

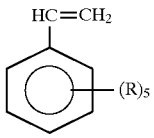

wherein each R is independently hydrogen; an aliphatic, cycloaliphatic or aromatic hydrocarbon group having from 1 to 10 carbon atoms; or a halogen atom.

9. The process according to claim 6 wherein the vinyl aromatic monomer is styrene.

10. The process according to claim 1 wherein M is titanium.

11. The process according to claim 1 wherein L is cyclopentadiene or pentamethylcycloppntadiene.

12. The process according to claim 1 wherein X each occurrence is R, $NR_2$ or OR.

* * * * *